United States Patent
Whitaker et al.

(10) Patent No.: US 11,837,345 B2
(45) Date of Patent: *Dec. 5, 2023

(54) SYSTEMS AND METHODS FOR SECURE PRESCRIPTION STATUS UPDATES USING A MOBILE DEVICE

(71) Applicant: WALGREEN CO., Deerfield, IL (US)

(72) Inventors: Lindsey Whitaker, Chicago, IL (US); Kevin David Meyer, Deerfield, IL (US)

(73) Assignee: WALGREEN CO., Deerfield, IL (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/357,716

(22) Filed: Jun. 24, 2021

(65) Prior Publication Data

US 2021/0319868 A1 Oct. 14, 2021

Related U.S. Application Data

(63) Continuation of application No. 15/172,960, filed on Jun. 3, 2016, now Pat. No. 11,081,214.

(51) Int. Cl.
*G16H 20/10* (2018.01)
*G16H 10/60* (2018.01)
(Continued)

(52) U.S. Cl.
CPC .......... *G16H 10/60* (2018.01); *G06F 21/6245* (2013.01); *G16H 20/10* (2018.01); *H04L 63/08* (2013.01); *H04L 63/10* (2013.01)

(58) Field of Classification Search
CPC ...... G16H 10/60; G16H 20/00; G06F 19/345; G06Q 50/22–24
See application file for complete search history.

(56) References Cited

U.S. PATENT DOCUMENTS 6,957,224 B1 * 10/2005 Megiddo ............. H04L 67/2814
6,988,075 B1  1/2006 Hacker
(Continued)

OTHER PUBLICATIONS

10 Mobile Must-Haves for Your Pharmacy; E Elements, Aug. 4, 2016 (Year: 2016).*

(Continued)

*Primary Examiner* — John A Pauls
(74) *Attorney, Agent, or Firm* — Randall G. Rueth

(57) ABSTRACT

A method of providing secure access to prescription information includes transmitting a text message including a short URL with a secure token to a device, receiving the secure token, transmitting to the device when the token matches, receiving a refill request; and transmitting a confirmation. A non-transitory computer readable storage medium includes computer-executable instructions that, when executed by a processor, cause a computer to determine a user of a device, provide a status including a short URL with a secure token, receive a short URL access request, validate the request; and provide authorized PHI access. A system includes a processor and a memory storing computer-executable instructions that, when executed by the processor, cause the system to determine a user corresponding to a device, provide a status including a short URL with a secure token, receive a short URL access request, validate the request; and provide authorized PHI access.

20 Claims, 6 Drawing Sheets

(51) Int. Cl.
*G06F 21/62* (2013.01)
*H04L 9/40* (2022.01)

(56) References Cited

U.S. PATENT DOCUMENTS

| | | |
|---|---|---|
| 8,452,608 B2 | 5/2013 | Smeeding et al. |
| 9,998,430 B2 | 6/2018 | Burch et al. |
| 10,210,311 B1 | 2/2019 | Taneja |
| 10,235,499 B1 | 3/2019 | Bleser et al. |
| 2003/0177040 A1 | 9/2003 | Birkhoelzer et al. |
| 2003/0212577 A1 | 11/2003 | Nichtberger |
| 2007/0061170 A1 | 3/2007 | Lorsch |
| 2007/0136279 A1* | 6/2007 | Zhou .................. G06F 16/9566 |
| 2007/0143139 A1 | 6/2007 | Ross et al. |
| 2008/0091544 A1 | 4/2008 | Linlor |
| 2012/0030736 A1 | 2/2012 | Resch et al. |
| 2012/0203571 A1 | 8/2012 | Crapo et al. |
| 2016/0364699 A1 | 12/2016 | Steketee et al. |
| 2017/0053066 A1 | 2/2017 | Kukreja et al. |

OTHER PUBLICATIONS

"Good Practices for Capability U RLs"; Tennison (Editor); W3C Tag Finding; Oct. 30, 2014 (Year: 2014).
Georgiev et al., "Gone in Six Characters: Short URLs Considered Harmful for Cloud Services," Cornell University (2016).
"Texting password reset links instead of a code"; Information Security Stack Exchange; Apr. 21, 2016; Fred (Year: 2016).

* cited by examiner

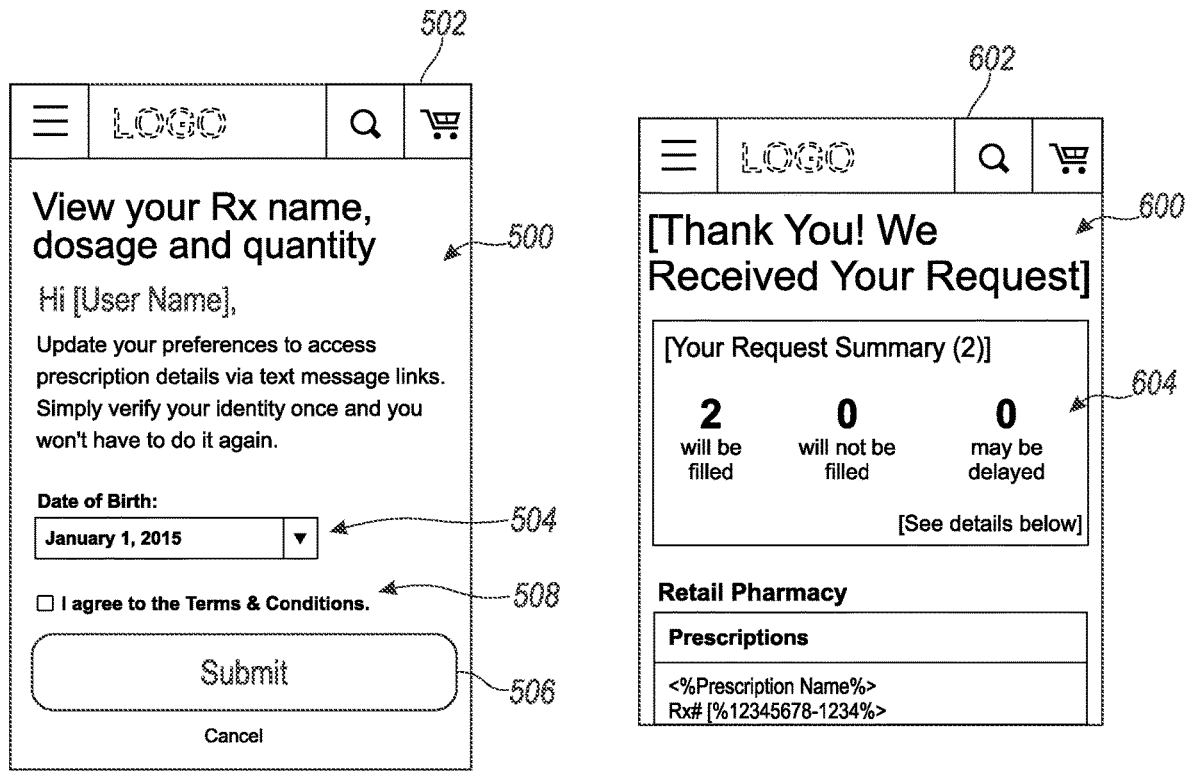
FIG. 5
FIG. 6
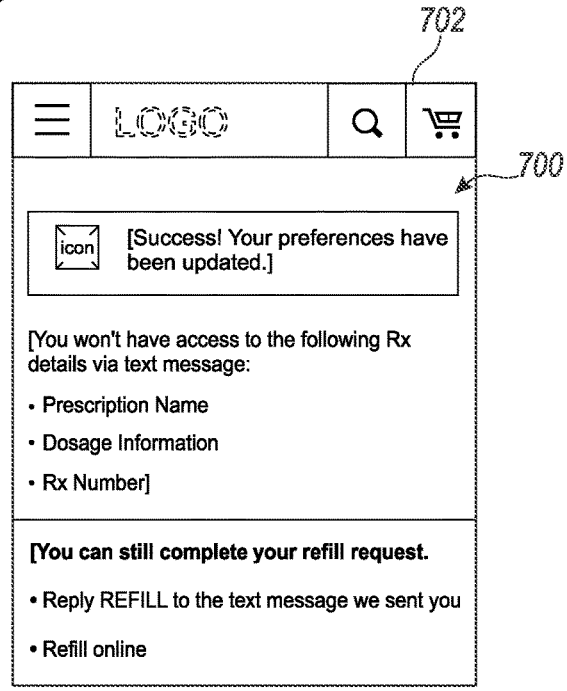
FIG. 7

SYSTEMS AND METHODS FOR SECURE PRESCRIPTION STATUS UPDATES USING A MOBILE DEVICE

CROSS-REFERENCE TO RELATED APPLICATIONS

This application is a continuation of U.S. patent application Ser. No. 15/172,960, filed on Jun. 3, 2016, entitled "SYSTEMS AND METHODS FOR SECURE PRESCRIPTION STATUS UPDATES USING A MOBILE DEVICE", the entire contents of which are hereby incorporated herein by reference.

TECHNICAL FIELD

This disclosure relates to prescription refills, and more particularly, to placing secure prescription refill orders using a mobile device.

BACKGROUND

Given the increasingly ubiquitous nature of mobile devices in today's world, many pharmacies provide mobile applications, websites, and/or other online systems for ordering and/or refilling prescriptions for drugs and other medicines. Existing systems typically require the user to log into, and/or register with, the online pharmacy system before allowing the user to place an order. The log-in process can require entry of a username and password, while the registration process can require setting up the same, as well as entry of additional identifying information. In addition, the user may be asked to provide information identifying the prescription medicine to be refilled. For example, the pharmacy system may prompt the user to scan, or otherwise capture an image of, a label on the prescription medicine container, select a prescription to refill from a list of past or existing prescriptions, and/or enter a prescription number or other information identifying the prescription. Thus, existing techniques for refilling a prescription using a mobile device can involve multiple steps before the user can place an order.

Another drawback of existing online pharmacy systems is the limited ability to send refill reminders to the mobile device of the user, due to government regulations designed to protect individual privacy. In particular, the current HIPAA Privacy Rule requires an individual's written authorization before his or her protected health information (PHI) can be used or disclosed to make a marketing communication to the individual. While the Privacy Rule expressly excludes refill reminders from the definition of "marketing" communications, subject to certain qualifications, the distribution of refill reminders in a mobile environment triggers the HIPAA Security Rule. The current Security Rule requires "covered entities," including pharmacies, to implement certain safeguards for securing electronic forms of PHI, or e-PHI, including security measures for controlling unauthorized access to, and maintaining the integrity of, e-PHI during transmission of this data over an electronic network.

Accordingly, there is still a need for an online pharmacy system that can provide refill reminders to mobile device customers in a secure and convenient manner, while complying with existing privacy regulations.

SUMMARY

In one aspect, a computer-implemented method of providing secure electronic access to prescription status information of a user includes (a) transmitting, via one or more processors, a text message including a short uniform resource locator (URL) to a mobile computing device associated with the user, wherein the short URL includes a secure authentication token; (b) receiving, in response to a selection of the user, the secure authentication token in a pharmacy system; (c) transmitting, when the secure authentication token matches stored authentication data, a prescription refill webpage to the mobile computing device; (d) receiving, in response to a selection of the user, a prescription refill order request in the pharmacy system; and (e) transmitting, in response to receiving the prescription refill order request, a refill order confirmation to the mobile device of the user.

In another aspect, a non-transitory computer readable storage medium includes computer-executable instructions that, when executed by one or more processors, cause a computer to: (i) determine, in response to receiving a status request message, a user corresponding to a mobile device associated with the status request message; (ii) provide, over a communication network, a refill status message comprising a short uniform resource locator (URL) to the mobile device associated with the status request message, wherein the short URL includes a secure authentication token; (iii) receive a request to access the short URL; (iv) validate the request based on stored authentication data; and (v) provide, over the communication network, access to the prescription status webpage on the mobile device upon obtaining authorization to electronically access protected health information (PHI) of the user.

In yet another aspect, a system in network communication with a mobile device of a user includes one or more processors and one or more memories storing computer-executable instructions that, when executed by the one or more processors, cause the system to: (i) determine, in response to receiving a status request message, an identity of the user corresponding the mobile device associated with the status request message; (ii) provide, over a communication network, a refill status message comprising a short uniform resource locator (URL) to the mobile device associated with the status request message, the short URL including a secure authentication token; (iii) upon receiving a request to access the short URL, validate the request based on stored authentication data; and (iv) provide, over the communication network, access to the prescription status webpage on the mobile device upon obtaining authorization to electronically access protected health information (PHI) of the user.

Other implementations are contemplated in accordance with the techniques described herein, as will be apparent to one having ordinary skill in the art upon examination of the following drawings and detail description, and such implementations are intended to within the scope of this disclosure.

BRIEF DESCRIPTION OF THE DRAWINGS

For a better understanding of the invention, reference may be made to the exemplary and non-limiting embodiments shown in the following drawings and described hereinafter. The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

FIG. 5 is a screenshot of an exemplary protected health information (PHI) access webpage displayed on a mobile device of the environment of FIG. 1, in accordance with embodiments.

FIG. 6 is a screenshot of an exemplary refill order confirmation webpage displayed on a mobile device of the environment of FIG. 1, in accordance with embodiments.

FIG. 7 is a screenshot of an exemplary PHI opt-out confirmation webpage displayed on a mobile device of the environment of FIG. 1, in accordance with embodiments.

DETAILED DESCRIPTION

Figure 1:
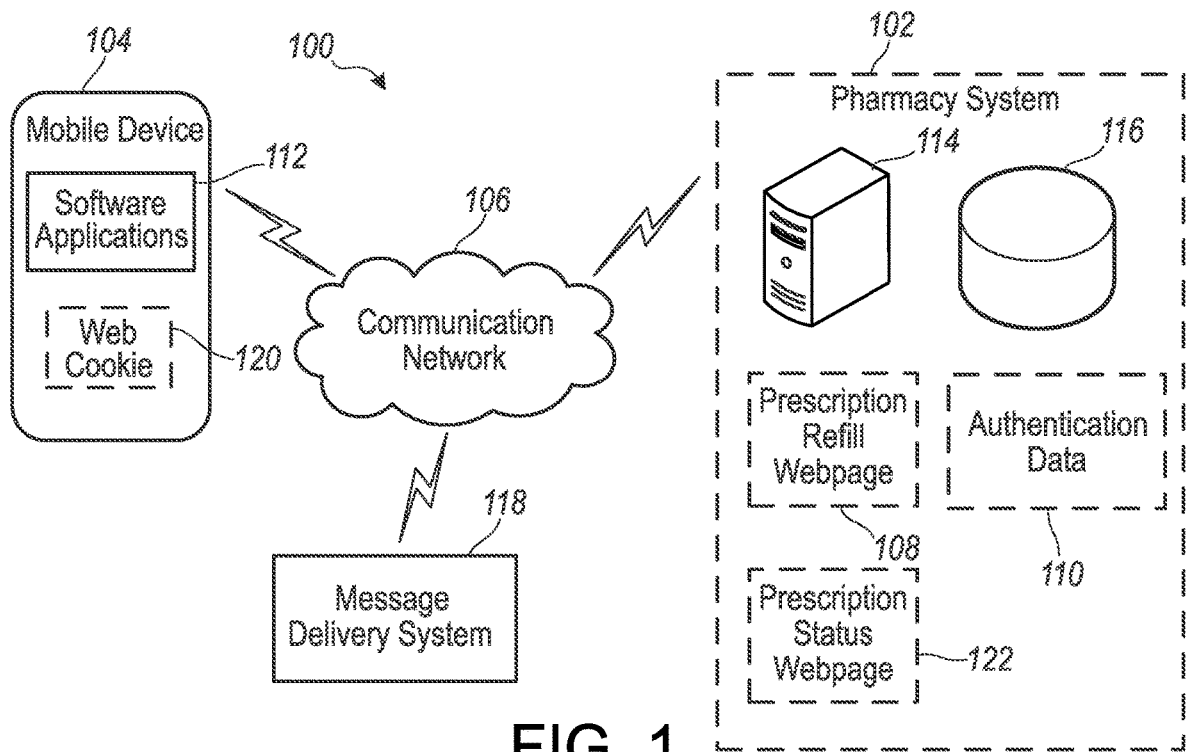
FIG. 1 is a block diagram illustrating an exemplary environment for providing secure access to prescription refill and status information on a mobile device, in accordance with embodiments.

The description that follows describes, illustrates, and exemplifies one or more particular embodiments of the invention in accordance with its principles. This description is not provided to limit the invention to the embodiments described herein, but rather to explain and teach the principles of the invention in such a way to enable one of ordinary skill in the art to understand these principles and, with that understanding, be able to apply them to practice not only the embodiments described herein, but also other embodiments that may come to mind in accordance with these principles. The scope of the invention is intended to cover all such embodiments that may fall within the scope of the appended claims, either literally or under the doctrine of equivalents.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects.

As used herein, the term "protected health information," or "PHI," refers to "individually identifiable health information, as defined by the HIPAA Privacy Rule. More specifically, PHI includes information that (1) identifies, or can be reasonably expected to identify, an individual, including demographic data and common identifiers (e.g., name, address, birth date, and Social Security Number), and (2) relates to an individual's past, present or future physical or mental health or condition; the provision of health care to the individual; or the past, present, or future payment for the provision of health care to the individual. In this disclosure, the PHI may be held and/or transmitted in electronic form and therefore, may also be referred to as "electronic-PHI" or "e-PHI."

As used herein, the term "short Uniform Resource Locator," or "short URL," refers to a uniform resource locator that has been shortened in length but still directs the requesting device to the webpage associated with the underlying URL. Short URLs may be generated by linking the originating web address, or "long URL," to a shortened domain name (e.g., "http://walgrn.com/") and a random string of characters, or unique key, that is uniquely associated with the intended destination but conceals the target address. A hash function or other security measures may be used to form the unique key, so that the key sequence is not predictable or easily reversible. In other cases, short URLs may be custom or vanity URLs that include, instead of a unique key, one or more terms to describe or preview the content of the underlying website. Each short URL may be stored in association with a corresponding long URL in a registry database. When a request to access the short URL is received, the registry database may be searched to locate the associated long URL, and the requesting device may be redirected to the webpage corresponding to the located URL. Existing URL shortening service providers include, for example, TinyURL, Bitly, and smartURL.

As used herein, the term "pharmacy" may include, for example, a single outlet or a plurality of outlets affiliated with one or more entities that are licensed to dispense prescribed pharmaceutical products, such as, for example, drugs, medicaments, durable medical equipment, and the like. In some cases, the pharmacy may provide or vend other products in addition to the prescribed pharmaceutical products. As an example, the pharmacy outlets may include one or more of a conventional retail store, space within a location operated by another commercial or not-for-profit entity (e.g., a discount store, hospital, school, nursing home, etc.), an outlet in proximity to a warehouse or distribution center, a call-in pharmacy, a long-term care pharmacy, a workplace/on-site pharmacy, and a specialty pharmacy.

As used herein, the terms "user," "patient," or "customer" are interchangeable and may refer to an individual who has been prescribed one or more pharmaceutical products, such as, for example, drugs, medicaments, durable medical equipment, or the like, or a representative of such individual. For example, the representative may be the individual's caregiver (e.g., parent or other family member) or other person authorized to interact with a pharmacy on behalf of the individual to, for example, fill or refill a prescription order and/or provide payment for said order.

FIG. 1 illustrates an exemplary environment 100 for providing secure electronic access to prescription refill information on, for example, a mobile computing device (also referred to herein as "mobile device"), in accordance with embodiments. As shown, the environment 100 includes a pharmacy system 102 in communication with a mobile device 104 via a communication network 106. The mobile device 104 is associated with, or operated by, a user that has a prescription refill need and is a customer of a pharmacy associated with the pharmacy system 102.

Figure 2:
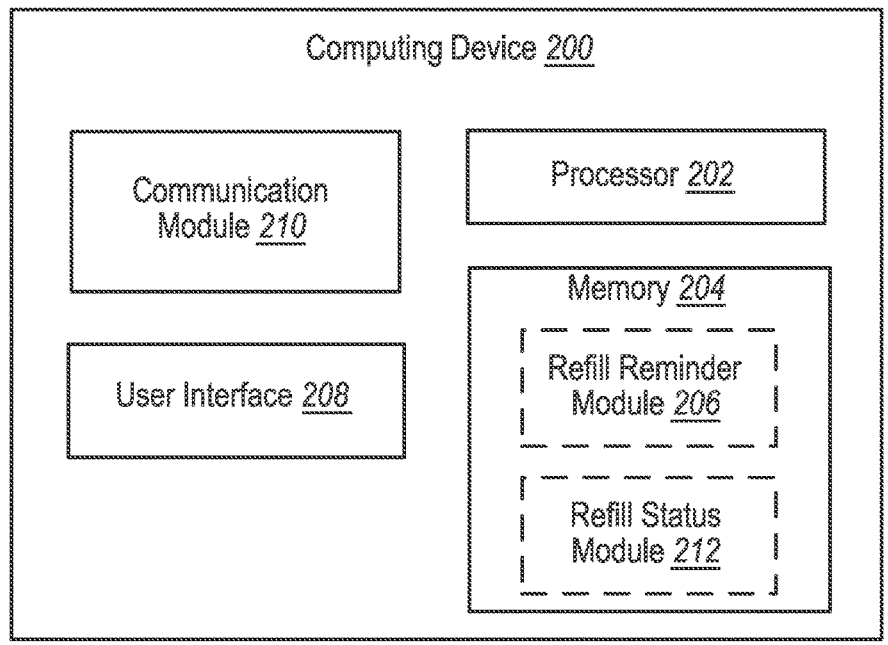
FIG. 2 is a block diagram of an example computing device of FIG. 1 for implementing various operations of the environment shown in FIG. 1, in accordance with embodiments.

Various components of the environment 100, and/or interactions there between, may be implemented using software executable by one or more servers or computers, such as exemplary computing device 200 with a processor 202 and a memory 204, as shown in FIG. 2 and described in more detail below. Moreover, certain interactions between the components of the environment 100 may include providing displayable content to the mobile device 104, and/or causing the mobile device 104 to display the same, in the form of web pages, text messages, prompts, and/or other notifications, for example, as illustrated by the exemplary screenshots shown in FIGS. 3 through 10.

For example, computing device 200 may be included in the pharmacy system 102 and may comprise a refill reminder module 206 stored in memory 204 and including software instructions that, when executed by processor 202, cause processor 202 to, among other things, (1) identify the user as having a prescription refill need; (2) generate an authentication token associated with the user; (3) generate a short uniform resource locator (URL) corresponding to a prescription refill webpage 108 associated with the user, and incorporating the authentication token; (4) provide, to the mobile device 104 via the communication network 106, a refill reminder alert or message comprising the short URL in a user-selectable hyperlink form (e.g., refill reminder text message 300 in FIG. 3); (5) validate a request to access the short URL received from the mobile device 104 based on stored authentication data 110, and (6) provide access to the prescription refill webpage 108 on the mobile device 104 (e.g., prescription refill webpage 400 in FIG. 4) upon obtaining authorization to electronically access protected health information (PHI) of the user (e.g., via PHI access webpage 500 in FIG. 5). These and other operations of the refill reminder module 206 are discussed in more detail below.

Additionally, the computing device 200 may comprise a refill status module 212 stored in the memory 204 and including software instructions that, when executed by the processor 202, cause the processor 202 to, among other things, (1) in response to receiving a request for a status of a prescription, identify user(s) corresponding to an identifier associated with the request; (2) generate an authentication token associated with the user; (3) generate a short uniform resource locator (URL) corresponding to a prescription status webpage 122 associated with the user, and incorporating the authentication token; (4) provide, to the mobile device 104 via the communication network 106, a refill status message comprising the short URL in a user-selectable hyperlink form (e.g., refill status text messages 802 of FIGS. 8 and 9 respectively); (5) validate a request to access the short URL received from the mobile device 104 based on stored authentication data 110, and (6) provide access to the prescription status webpage 122 on the mobile device 104 (e.g., prescription status webpage 1000 of FIG. 10) upon obtaining authorization to electronically access protected health information (PHI) of the user (e.g., via PHI access webpage 500 of FIG. 5). These and other operations of the refill status module 212 are discussed in more detail below.

For the sake of simplicity, FIG. 1 only shows one mobile device 104. However, it will be appreciated that the environment 100 may include a plurality of mobile devices respectively associated with each customer having a prescription refill need and similar to the mobile device 104 described herein. In embodiments, each mobile device 104 may be implemented as user equipment (UE), such as, for example, a smartphone, or any other suitable communication device configured to communicate or interact with the other components of the environment 100 via the communication network 106 using one or more wired and/or wireless links for sending data to and/or receiving data from said components. For example, the mobile device 104 may be implemented as a portable computing device, a personal digital assistant (PDA), a tablet computer, a laptop computer, a wearable electronic device, etc. As will be appreciated, the mobile device 104 may be associated with a unique phone number, as well as other numbers or indicia for identifying the mobile device 104, including, for example, a media access control (MAC) address or Internet Protocol (IP) address, a mobile directory number, a serial number (e.g., a Electronic Serial Number (ESN), a Mobile Equipment Identifier (MEID), a International Mobile Station Equipment Identity (IMEI), etc.), a subscriber or local routing number (LRN), and/or mobile identification number (MIN).

The mobile device 104 can include hardware devices (e.g., a display, a communication module, and a user interface) and one or more software applications 112 for facilitating interactions with, and/or presenting content received from, other components of the environment 100. In embodiments, the one or more software applications 112 can include a mobile messaging application (not shown) configured to send and receive text and/or voice messages and display the same in a graphical user interface of the mobile messaging application. For example, the mobile messaging application may be used to present text messages received from the pharmacy system 102, such as the refill reminder text message 300 of FIG. 3 and/or the refill status text messages 802 of FIGS. 8 and 9. In some cases, the mobile messaging application may be a traditional short message service (SMS) text messaging application that is native to the mobile device 104 and is capable of sending and receiving messages over a cellular and/or Internet (e.g., WiFi) connection via the communication network 106. In such cases, the mobile messaging application may be tied to the phone number of the mobile device 104. In other cases, the mobile messaging application may be an alternative instant messaging application that is downloaded to the mobile device 104 and is capable of sending and receiving messages over an Internet connection via the communication network 106.

The one or more software applications 112 can also include a mobile email application (not shown) configured to send and receive emails and display the same in a graphical user interface of the mobile email application. For example, in some embodiments, the pharmacy system 102 can be configured to send a refill reminder email instead of the text message 300 and/or a prescription status email instead of the refill status text messages 802 of FIGS. 8 and 9. In such embodiments, the mobile email application may be used to present the refill reminder email and/or the prescription status email on a display of the mobile device 104.

In embodiments the one or more software applications 112 also include a web browser that is stored in and operating on the mobile device 104 and can be used to access a website hosted by the pharmacy system 102 and/or load one or more web pages associated therewith. For example, the prescription refill webpage 108 and/or the prescription status webpage 122 may be loaded into the web browser of the mobile device 104. In some cases, the one or more software applications 112 may also include a mobile application that is at least partially stored in, and operating on, the mobile device 104 and is associated with, or native to, the pharmacy system 102, such as a pharmacy application for accessing prescription information, placing prescription orders, purchasing other items from the pharmacy, etc. In such cases, the prescription refill webpage 108, the prescription status webpage 122 and any other webpage provided by the pharmacy system 102 may be displayed in a graphical user interface of the mobile application as an application page.

The communication network 106 may include any suitable number of wired and/or wireless networks, including, for example, a local area network (LAN), a metropolitan area network (MAN), a wide area network (WAN), or a combination of local and/or external data networks. As a further example, the communication network 106 may include wired telephone and/or cable networks, satellite networks, cellular communication networks, and the like. In embodiments, the communication network 106 can be configured to provide the mobile device 104, the pharmacy system 102, and any other component of the environment 100 with connectivity to network services, such as Internet services.

The pharmacy system 102 may include any suitable number of components that are owned and/or operated by the pharmacy and are configured to implement these and other operations of the environment 100, as described herein. For example, the pharmacy system 102 can include one or more servers 114, databases 116, and/or other computing devices. The components of the pharmacy system 102 may communicate with each other using any suitable number of wired and/or wireless links, including via the communication network 106. As will be appreciated by those of ordinary skill in the relevant art(s), the pharmacy system 102 may store, access, and/or transmit secure data that is of a private, proprietary, and/or sensitive nature. As a result, various embodiments of the pharmacy system 102, as well as the communication network 106, the mobile device 104, and/or other components of the environment 100, may implement appropriate security protocols such as encryption, secure links, network authentication, firewalls, etc., to appropriately protect such secure data.

Server 114 may be implemented as, for example, any suitable number of web servers configured to provide Internet communications to one or more mobile computing devices of the environment 100, such as the mobile device 104, to process application programming interface (API) service calls, and/or to support one or more applications installed on a computing device (such as, e.g., computing device 200) of the pharmacy system 102. In addition, or alternatively, server 114 may be implemented as, for example, as any suitable number of database servers configured to access data from database 116.

Database 116 may be configured to store any relevant data related to operation of the environment 100. Such data may include, for example, customer profile data that includes customer information (e.g., name; mailing address, email address, mobile phone number, home phone number, and/or other contact information; date of birth; Social Security Number; a patient identification (ID) number, a member ID number, or other identifying information; family members and/or care recipients that have authorized the customer to interact with the pharmacy on their behalf; family members, care givers, and/or representatives authorized to interact with the pharmacy on behalf of the customer; etc.), payment information (e.g., credit card information, debit card information, etc.), prescription information (e.g., for each prescription, a prescription name, a prescription ID or number, a type, classification, quantity, and/or dosage of the prescription, a name of the prescriber, a number of available refills (if any), an expiration date for available refills, etc.), insurance information, and any other protected health information (PHI) for each customer of a pharmacy. One or more components of the pharmacy system 102, such as server 114, may communicate with database 116 to store data to and/or read data from database 116, as needed to facilitate appropriate functions of the embodiments described herein.

In embodiments, the pharmacy system 102, or the refill reminder module 206 included therein, can be configured to identify one or more customers having a prescription refill need based on, for example, the customer profile data or any other data stored in database 116. For example, based on the customer profile data, the refill reminder module 206 may determine a prescription refill need for a given patient based on the prescription dosage information (e.g., number of units per dose, number of doses per day, etc.), the prescription quantity information (e.g., number of units in one container), the number of available refills (if any), and the expiration date of available refills for each drug or medicament currently prescribed to the patient. Moreover, one or more business rules may determine how far in advance of the refill due date to generate a refill reminder (e.g., one week, three days, etc.). In some cases, the refill reminder module 206 may periodically query the database 116 to retrieve a batch of prescriptions that have refills due and are associated with various customers. As will be appreciated, some customers may have only one prescription refill due at the time of the query, while other customers may have multiple prescription refills due. In the case of customers that manage prescriptions for one or more other patients, such as family members or care recipients, the identified prescription refills may include prescriptions for these other patients, as well as those for the customer.

Also according to embodiments, for each customer identified as having at least one prescription refill need, the pharmacy system 102 and/or the refill reminder module 206 can be configured to generate a refill reminder message and provide the message to the mobile computing device of the corresponding customer. The refill reminder message may be, for example, an SMS text message that is sent to the mobile number associated with the mobile device 104, or an email message that is either sent to an email address of the customer or delivered as a text message to the mobile device 104. In embodiments, the refill reminder message can be configured to include a generic set of information that (1) identifies the pharmacy that is sending the message, (2) informs the customer that a prescription refill is due, and (3) provides one or more options for ordering the refill that is due, but does not reveal the identifying information or other PHI of the customer.

In embodiments, the pharmacy system 102, or the refill status module 212 included therein, can be configured to respond to a request for a status of a user's prescription based on, for example, (i) an identifier associated with the status request, and (ii) the customer profile data or any other data stored in database 116. The status request is a text message or an email sent by the mobile device 104 that includes a keyword, defined by the pharmacy system 102, that is associated with requesting status of a customer's prescriptions. For example, the keyword may be "RXSTATUS." The identifier is the indicia for identifying the mobile device 104 (e.g., the MAC address or IP address, the mobile directory number, the LRN, and/or the MIN) that sent the request. In some examples, the pharmacy system 102, or the refill status module 212 determines whether the user(s) associated with the mobile device 104 has/have granted PHI authorization (e.g. via the e.g., PHI access webpage 500 of FIG. 5). In such examples, if the user(s) associated with the mobile device 104 has/have granted PHI authorization, the pharmacy system 102, or the refill status module 212 continue to process the status request. Otherwise in such examples, if the user(s) associated with the mobile device 104 has/have not granted PHI authorization, the pharmacy system 102, or the refill status module 212 may (a) ignores the status request, or (b) sends a message with a short URL that directs that user to the PHI access webpage.

In response to receiving the status request, the refill status module 212 compares the identifier to the customer profile data stored in database 116 to determine which customer sent the status request. In some examples, more than one customer is associated with the identifier. For example, a husband and wife may have registered with the pharmacy system 102 using the same mobile device 104. In such examples, the refill status module 212 assigns a temporary identifier to the customers associated with the same mobile device 104. For example, the temporary identifier may be "1" and "2." As another example, the temporary identifier may be an alias (such as, "Bunny," "Steven1984," etc.) created by the customer when the customer registered a prescription with the pharmacy. The refill status module 212 sends a clarification message (e.g., the clarification message 900 of FIG. 9) or a clarification email to the mobile device 104 configured to include (a) customer identifiers (e.g., names, etc.), (b) the corresponding temporary identifiers, and (c) a request that the user send a text message or an email with the temporary identifier corresponding to the user.

If there is only one customer associated with the mobile device 104 or the refill status module 212 receives a clarification reply message with one of the temporary identifiers, the refill status module 212 sends the refill status message configured to include (1) one or more status categories (e.g., "action required," "delayed," "ready," "in process," etc.) and a number of prescriptions in those status categories, and (2) a short URL that, when browsed to, navigates software application 112 of the mobile device 104 to the prescription status webpage 122 associated with that customer. However, in some examples, the refill status message does not include information (e.g., medicine names, medicine serial numbers, etc.) that identifies which prescriptions are associated with the customer. The status message may be, for example, an SMS text message that is sent to the mobile number associated with the mobile device 104, or an email message that is either sent to an email address of the customer or delivered as a text message to the mobile device 104.

In some examples, the pharmacy system 102 and/or the refill status module 212, from time to time (e.g., hourly, daily, weekly, etc.), may analyze the customer profile data or any other data stored in database 116 to determine if a status of a prescription has changed (e.g. the status update event). For example, the status of a prescription may change from "pending" to "ready" or from "pending" to "action required," etc. In such examples, for each customer identified as having at least one prescription with a status update event, the pharmacy system 102 and/or the refill status module 212 can be configured to generate a status message and provide the message to the mobile computing device of the corresponding customer. In such examples, the status message can be configured to include a generic set of information that (1) identifies the pharmacy that is sending the message, (2) informs the customer that one or more status categories (e.g., "action required," "delayed," "ready," "in process," etc.) have changed and a number of prescriptions in those status categories and (3) provides one or more options for receiving more information about the status change event, but does not reveal the identifying information or other PHI of the customer.

Figures 3, 4:
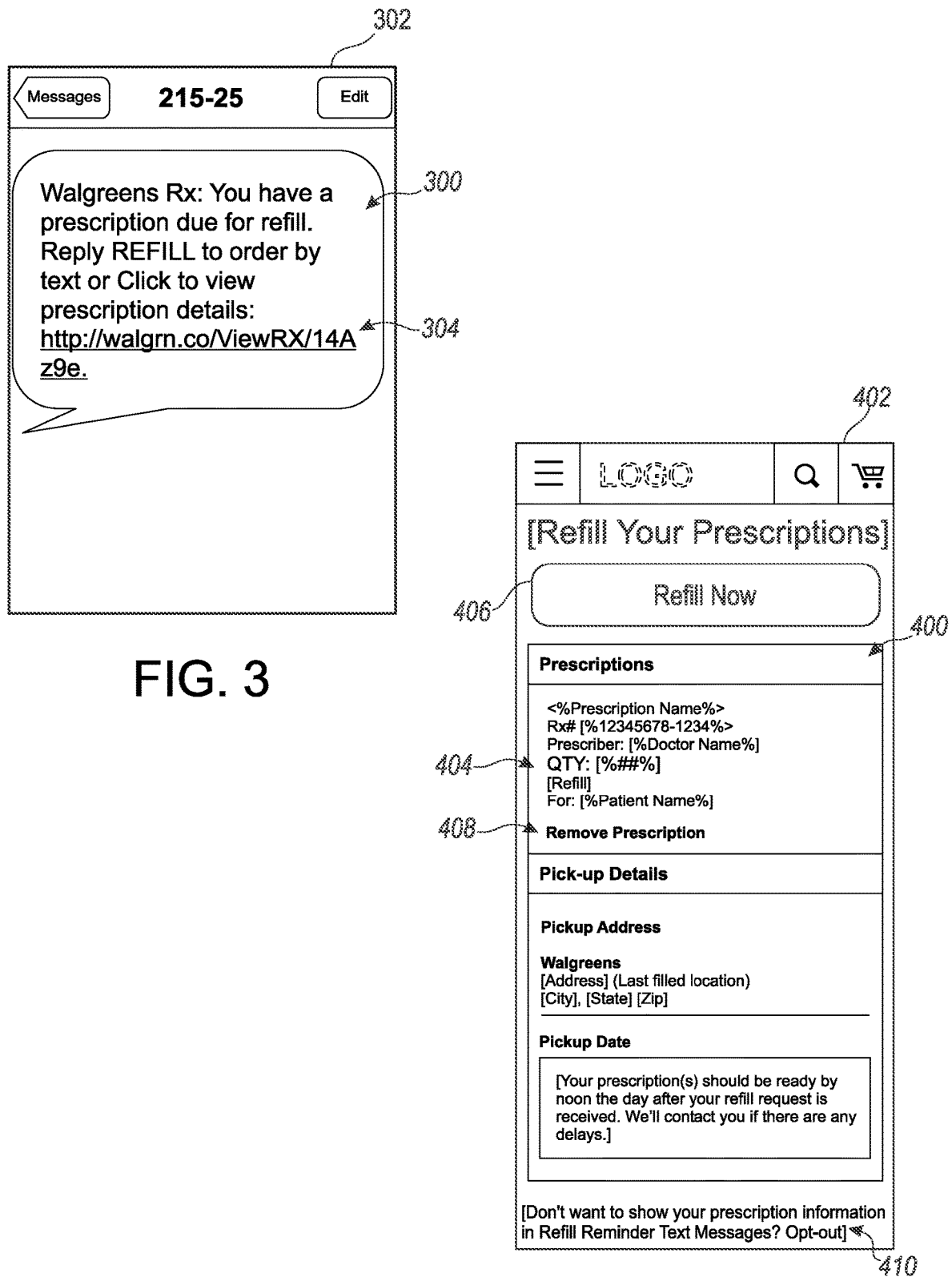
FIG. 3 is a screenshot of an exemplary refill reminder text message displayed on a mobile device of the environment of FIG. 1, in accordance with embodiments.
FIG. 4 is a screenshot of an exemplary prescription refill webpage displayed on a mobile device of the environment of FIG. 1, in accordance with embodiments.

For example, FIG. 3 illustrates a screenshot of an exemplary refill reminder message 300 displayed on a display screen 302 of a mobile computing device, such as the mobile device 104, in accordance with embodiments. As shown, the refill reminder message 300 may be displayed in the graphical user interface of a mobile messaging application of the mobile device 104. As also shown, the content of the refill reminder message 300 simply states: "You have a prescription due for refill," without specifying details regarding the prescription or patient tied thereto. In response, the customer has the option of replying "REFILL" to order a prescription refill via text message, or clicking on a user-selectable short URL, or hyperlink, 304 to view the prescription details in an external webpage before placing a refill order. The short URL of the hyperlink 304 can be configured to direct the customer to the prescription refill webpage 108 associated with the customer, such as, for example, the prescription refill webpage 400 shown in FIG. 4.

In embodiments, the pharmacy system 102 can be configured to generate the short URL for each refill reminder message based on a web address for the prescription refill webpage 108 associated with each customer. For example, the web address of the prescription refill webpage 108 may be a long URL that contains an original domain name associated with the pharmacy system 102 and a string of address information for identifying the specific webpage 108. The short URL may contain a shortened domain name and a short string of characters that are uniquely associated with the prescription refill webpage 108. In some cases, the string of characters used for the short URL is randomly assigned to form a unique key. In other cases, at least a portion of the string of characters is customized according to criteria specified by the pharmacy. For example, in one embodiment, the first two characters of the string are encoded to signify the originating campaign or channel for which the short URL was generated (e.g., refill reminder text messages).

The short URL may be mapped to the long URL in a registry database that is stored in a memory of the pharmacy system 102 or other component (e.g., web server) of the environment 100, such that when a user requests access to the short URL, the user may be redirected to the long URL associated therewith. In some embodiments, the pharmacy system 102 includes a short URL generator comprising one or more algorithms for shortening the original web address of each prescription refill webpage and mapping the short URLs to corresponding long URLs. In other embodiments, the pharmacy system 102 provides the information required to generate the short URL to third-party provider, such as a URL shortening service, to generate the short URLs and provide the same back to the pharmacy system 102 for distribution to corresponding customers.

In embodiments, the web address of the prescription refill webpage 108 may be a dynamic URL that pulls data stored in a database, such as, for example, customer profile data stored in database 116, to personalize the content of the prescription refill webpage 108 for a given user. In such cases, the pharmacy system 102 and/or the refill reminder module 206 can be configured to apply additional security measures to the short URL so as to protect the dynamic URL from unauthorized access. For example, the short URL may be embedded with, or generated based on, a secure authentication token that is associated with the user and stored in the authentication data 110 shown in FIG. 1, as described in more detail herein. When a request to access the short URL (or the web address associated therewith) is received by the pharmacy system 102, the pharmacy system 102 and/or refill reminder module 206 may validate the request by comparing authentication information included in the request to the stored authentication data 110 before providing access to the prescription refill webpage 108.

In embodiments, to generate the contents of each refill reminder message, the pharmacy system 102 and/or the refill reminder module 206 can be configured to retrieve customer profile data from database 116. For example, the refill reminder module 206 may retrieve a mobile number, an email address, or other contact information of the customer that can be used to send the refill reminder to the mobile device of the customer. In addition, the refill reminder module 206 may retrieve a patient ID number and/or other identifying information that uniquely identifies the customer and/or the customer's account within the pharmacy system 102. For example, in some cases, the refill reminder module 206 may assign a patient ID number to each patient of the pharmacy and a member ID number to each member of a loyalty program of the pharmacy. In such cases, customers that are both patients and loyalty members of the pharmacy may have multiple pieces of identifying information stored in the database 116 (e.g., a patient ID number and a member ID number).

In addition, the refill reminder module 206 may assign a reminder identifier (ID) to each refill reminder message to help identify the particular contents of the message, such as, for example, which prescription refill due dates triggered that specific reminder message. The reminder ID may be stored in a look-up table and/or in the authentication data 110 in association with other content of the corresponding refill reminder message, as described in more detail below. The reminder ID may comprise an alphanumeric string of characters that is uniquely associated with the refill reminder message.

In embodiments, the pharmacy system 102 and/or the refill reminder module 206 can be configured to generate the secure authentication token for each refill reminder message based on the customer profile data (e.g., the identifying information and/or contact information) retrieved from database 116 and/or the reminder ID generated for that specific message. For example, the pharmacy system 102 may provide the customer profile data and/or reminder ID to a token generator comprising one or more software algorithms for encrypting, encoding, and/or hashing the information, or otherwise transforming the customer's information into a format that can be securely transmitted within the environment 100. In one embodiment, the token generator encrypts the reminder ID and/or the patient ID number, as well as the mobile number for each customer having a prescription refill need, produces a hash of the encrypted data, and encodes the encrypted data and the hash value into a character string to form the authentication token. In some cases, the token generator also includes a time-expiration algorithm for assigning an expiration date to the token and embedding the expiration date into the token.

The pharmacy system 102 and/or refill reminder module 206 may store the authentication token produced by the token generator in a look-up table that maps the authentication token to the pieces of information used to generate the token (e.g., the reminder ID, patient ID number, mobile number, expiration date, and/or hash value associated with the token) and to the short URL that is generated for the corresponding customer. In some cases, the look-up table may also include entries for other information related to generation and/or distribution of the refill reminder message, such as, for example, additional contact information (e.g., email address), a name of the customer, or other customer profile data. The look-up table may be included in the authentication data 110 shown in FIG. 1, as described in more detail below.

As shown in FIG. 1, the environment 100 may further include a message delivery system 118 for distributing the refill reminder message to respective customers, or more specifically, the mobile device associated with each customer, in accordance with instructions received from the pharmacy system 102. The message delivery system 118 may be a third-party provider of message distribution services or an affiliate of the pharmacy system 102. The message delivery system 118 may communicate with the other components of the environment 100 using one or more wired and/or wireless links via the communication network 106. In some cases, the message delivery system 118 may use a first communication protocol (e.g., a cellular network connection) to communicate with the mobile device 104 and a second communication protocol (e.g., an Internet or other wireless network connection) to communicate with the pharmacy system 102.

In embodiments, the pharmacy system 102 and/or the refill reminder module 206 may provide the look-up table to the message delivery system 118 for use in generating and distributing the refill reminder messages. For example, the message delivery system 118 may generate and deliver the refill reminder message 300 shown in FIG. 3 to the corresponding customer by (1) retrieving the short URL "http://walgrn.co/ViewRX/14Az9e" from the look-up table, (2) inserting the short URL, as an activate hyperlink 304, into a message template comprising the generic message contents shown in FIG. 3, (3) retrieving the mobile number associated with the short URL from the look-up table, and (4) send the refill reminder message as either an SMS text message or an email message to the retrieved mobile number.

According to embodiments, the authentication data 110 can be stored, all or in part, in one or more components of the pharmacy system 102, such as in a memory of server 114 and/or in database 116. The authentication data 110 may include, for each customer having a prescription refill need, the reminder ID of the refill reminder message; the authentication token generated for the customer; data related to the authentication token, including the hash value associated with the token and the expiration date of the token; the mobile phone number and/or other contact information of the customer; the patient ID number and/or other identifying information of the customer; a web address for the prescription refill webpage 108 associated with the customer (also referred to herein as "an intended destination"); the short URL generated based on the corresponding authentication token and web address; and any other suitable information related to the refill reminder message. All or a portion of the authentication data 110 may be stored in a data table, such as the look-up table described above.

The authentication data 110 can be used to validate any short URL requests received by the pharmacy system 102 to ensure that the short URL included in the request has not been tampered or otherwise altered. For example, when the customer clicks on the short URL hyperlink 304, a request to access the short URL included therein may be sent to the pharmacy system 102. The request may include the short URL and the authentication token embedded therein, including the hash value associated with the token. The pharmacy system 102 and/or the refill reminder module 206 may validate the received request by comparing the information included in the request to corresponding information included in the stored authentication data 110. For example, the pharmacy system 102 and/or the refill reminder module

206 may use a matching engine (not shown) to compare the received hash value to the hash value that is stored in the authentication data 110 for the corresponding short URL. In addition, the pharmacy system 102 and/or the refill reminder module 206 may determine whether the received token has expired based on the expiration date that is stored in the authentication data 110 for the corresponding authentication token. If the received authentication information is found to be valid and/or the authentication token has not expired, the pharmacy system 102 and/or the refill reminder module 206 may determine that the short URL request is valid and may proceed with processing the request (e.g., providing access to the intended destination). As will be appreciated, in other embodiments, other techniques and/or security measures may be used to validate the short URL request.

In embodiments, once the short URL request is determined to be valid, the pharmacy system 102 and/or the refill reminder module 206 can be configured to obtain authorization to electronically access the protected health information (PHI) of the corresponding customer, before providing the prescription refill webpage 108 to the mobile device 104. In some cases, this authorization may be obtained by checking the customer profile data of the customer to see if authorization was previously obtained. In other cases, the authorization may be obtained based on the content of the short URL request, for example, where the request includes a web cookie indicating that authorization was previously obtained for this customer, as described in more detail below.

In still other cases, the authorization may be obtained by providing a PHI access webpage to the mobile device 104 that prompts the customer to authorize electronic access to, and display of, the customer's prescription details via text message links (such as, e.g., the short URL hyperlink 304 shown in FIG. 3). The PHI access webpage may also request the customer to verify his/her identity as part of the authorization process, to ensure that the person requesting access to the short URL is the customer associated with the prescription refill. Identity verification may be performed using any number of suitable authentication techniques, including requesting the customer to provide information that is uniquely associated with the customer and stored in the customer's profile in database 116.

For example, FIG. 5 illustrates a screenshot of an exemplary PHI access webpage 500 displayed on a display screen 502 of a mobile computing device, such as the mobile device 104, in accordance with embodiments. In the illustrated embodiment, the PHI access webpage 500 includes an identity verification prompt 504 that requests the customer to enter his/her date of birth. In other embodiments, the identity verification prompt 504 may request entry of other verifiable identity information, such as, for example, a name of the customer, a username or user ID, all or a portion of a credit card number or a social security number, or other data stored in the customer's profile. In still other embodiments, the identity verification prompt 504 may involve use of knowledge-based authentication, two-factor authentication, or other identity verification techniques.

As shown in FIG. 5, the PHI access webpage 500 further includes a submit option 506. User-selection of the submit option 506 may send information entered into the identity verification prompt 504 to the pharmacy system 102. The pharmacy 102 and/or the refill reminder module 206 may include a matching engine (not shown) to determine whether the received information (e.g., date of birth) matches the information stored in the customer's profile, thereby verifying the customer's identity. In some cases, the PHI access webpage 500 may also include a "terms & conditions" check box 508, as well as the terms and conditions (not shown) associated with authorizing electronic access to, and display of, the customer's prescription details via text message links. User selection of the check box 508 may indicate that the customer accepts the terms and conditions posted on the PHI access webpage 500. In some cases, the check box 508 must be selected before the submit option 506 can be selected.

Once the terms & conditions check box 508 and/or the submit option 506 are selected, and the customer's identity is successfully verified, the pharmacy system 102 and/or the refill reminder module 206 may assign an "opt-in" status to a PHI indicator field within the customer profile data stored in database 116 for that customer. In embodiments, the above PHI authorization process may be performed only once, such as, for example, the first time the customer clicks on the short URL hyperlink 304 in the refill reminder message 300, and the next time the customer receives a refill reminder message, the pharmacy system 102 and/or the refill reminder module 206 may use a different process to obtain the PHI authorization. For example, in some embodiments, upon validating a short URL request, the pharmacy system 102 and/or the refill reminder module 206 may refer to database 116 to determine whether an opt-in status is stored in the customer's profile, and if it is, may determine that PHI authorization has been obtained.

As another example, in other embodiments, after storing the opt-in status in the PHI indicator field of the customer profile and/or verifying the customer's identity, the pharmacy system 102 and/or the refill reminder module 206 can be configured to generate a web cookie 120 indicating the opt-in status of the user. The pharmacy system 102 may send the web cookie 120 to the mobile device 104, via the communication network 106, for storage therein and future retrieval therefrom, as shown in FIG. 1. For example, after the initial short URL request, the web cookie 120 may be stored in the web browser and/or the pharmacy application of the mobile device 104 and may be presented to the pharmacy system 102 with each short URL request thereafter. The web cookie 120 (also referred to as an "HTTP cookie") may comprise an authentication token or other security measures for ensuring the authenticity of the cookie 120. The web cookie 120 may be stored in the authentication data 110 (e.g., in the look-up table) in association with the corresponding customer's other data (e.g., patient ID number, phone number, short URL, etc.). Upon receiving a short URL request that includes the cookie 120, the pharmacy system 102 and/or the refill reminder module 206 may validate the received cookie based on the stored web cookie information, and if the cookie 120 is valid, may determine that authorization for PHI access via text message links has been obtained.

Upon obtaining authorization to electronically access the PHI of the customer via text message links, the pharmacy system 102 and/or the refill reminder module 206 may provide access to the prescription refill webpage 108 on the mobile device 104 via the communication network 106. For example, the pharmacy system 102 may send the prescription refill webpage 108 to the mobile device 104 for presentation within the web browser and/or pharmacy application of the mobile device 104. The prescription refill webpage 108 can be stored, all or in part, in one or more components of the pharmacy system 102, such as in a memory of server 114 and/or in database 116. In some cases, the prescription refill webpage 108 may be dynamically generated or personalized for each user by retrieving appropriate data from database 116, such as, customer profile data for the user, using, for example, the computing device 200 in FIG. 2. In such cases, appropriate security measures may be employed to ensure that the content of the prescription refill webpage 108 is not publically searchable. In some embodiments, the prescription refill webpage 108 can be implemented as an adaptive webpage that is configured to detect the mobile device 104 and optimize the webpage 108 for the mobile device 104 based on certain features of the mobile device 104 (e.g., screen size and/or device type). As will be appreciated, other suitable techniques for implementing the prescription refill webpage 108 may be utilized.

FIG. 4 illustrates a screenshot of an exemplary prescription refill webpage 400 displayed on a display 402 of a mobile computing device, such as the mobile device 104, in accordance with embodiments. As shown, the prescription refill webpage 400 displays prescription information 404 for at least one drug, medicament, or medical device that is currently-prescribed to the user, or a patient associated with the user (e.g., a family member), and is due for a refill. As will be appreciated, though FIG. 4 only shows one active prescription, the prescription refill webpage 400 may include additional prescription information for each prescription that is due for a refill. The prescription refill webpage 400 also displays a user-selectable "refill now" option 406 for submitting an order to refill the prescription(s) listed on the refill webpage 400. Once the user selects the refill now option 406 on the mobile device 104, a prescription refill order may be submitted to the pharmacy system 102, and in response, the pharmacy system 102 may send an order confirmation notification back to the mobile device 104. For example, in some cases, the pharmacy system 102 may send the refill order confirmation as an SMS text message to the mobile number of the mobile device 104. In other cases, the pharmacy system 102 may send the refill order confirmation as a webpage that is presented by the web browser and/or pharmacy application of the mobile device 104.

FIG. 6 illustrates a screenshot of an exemplary refill order confirmation webpage 600 displayed on a display 602 of a mobile computing device, such as the mobile device 104, in accordance with embodiments. The order confirmation webpage 600 may list the details of each prescription refill that was ordered, including where and when the prescription refill order can be picked up. As shown, the order confirmation webpage 600 may also display an order fulfillment summary 604 that shows whether or not the prescription refill order was accepted by the pharmacy and whether there will be a delay in filling the order.

Once the refill order is submitted, the pharmacy system 102 and/or the refill reminder module 206 may update the web cookie 120 and send the updated cookie to the mobile device 104 for storage therein. In addition, the pharmacy system 102 and/or the refill reminder module 206 may store the updated cookie in the authentication data 110 in place of the existing cookie 120, or synch the existing cookie 120 with the updated cookie information. For example, the web cookie 120 may be updated to reset an inactivity counter embedded into the cookie 120, update an IP address associated with the mobile device 104, or advance an expiration date associated with the authentication token included in the cookie 120.

Referring back to FIG. 4, as shown, the prescription refill webpage 400 may include a "remove prescription" option 408 for each prescription listed on the webpage 400. The option 408 may be selected by the customer to remove prescriptions that the customer does not want to refill from the refill order. For example, the customer may want to refill only one of two prescriptions displayed on the webpage 400. In embodiments, the prescription refill webpage 400 may be configured to display only those prescriptions that have a refill due. If the customer wishes to add other prescriptions to the order, the pharmacy system 102 may require the customer to log into the main pharmacy website, or access a different part of the pharmacy application, to view additional prescription details and/or place additional orders.

In embodiments, the customer may also be presented with an option to "opt-out" from providing authorization for electronic access to the PHI of the user via text message links. For example, as shown in FIG. 4, the prescription refill webpage 400 may include an "opt-out" option 410 that may be selected if the customer does not want his/her prescription information to be shown in, or accessible via, refill reminder messages. Though the opt-out option 410 is only shown on the webpage 400, it may also be presented on other webpages or prompts provided to the mobile device 104, including, for example, the refill order confirmation webpage 600 and/or the PHI access authorization webpage 500.

If the customer selects the opt-out option 410, the pharmacy system 102 and/or the refill reminder module 206 may assign an "opt-out" status to the PHI indicator field of the customer profile data stored in database 116 for that customer. In addition, the pharmacy system 102 may send an opt-out confirmation notification to the mobile device 104, via the communication network 106, to confirm the opt-out status selection. For example, the opt-out confirmation notification may be sent as an SMS text message the mobile number of the mobile device 104. As another example, the pharmacy system 102 may send the opt-out confirmation notification as a webpage that is presented in the web browser and/or pharmacy application of the mobile device 104.

FIG. 7 illustrates a screenshot of an exemplary opt-out confirmation webpage 700 displayed on a display 702 of a mobile computing device, such as the mobile device 104, in accordance with embodiments. As shown, the opt-out confirmation webpage 700 may inform the customer of the information that will no longer be shown via text message, such as, for example, prescription name, dosage information, and prescription (Rx) number. As also shown in FIG. 7, even after opting-out of PHI authorization, the customer may still have other options for ordering prescription refills via text message (e.g., text "REFILL" in reply to the original refill reminder message) or by logging into the main pharmacy website (e.g., refill online).

Referring now to FIG. 2, shown is a block diagram of computing device 200 housing executable software used to facilitate interactions between components of the environment 100, in accordance with embodiments. In particular, one or more instances of the computing device 200 may be utilized to implement any, some, or all of the components in the pharmacy system 102, such as, for example, server 114, database 116, and/or a proprietary pharmacy computer system (not shown), such as, for example, Walgreen Company's Intercom Plus (IC+) computer system. Because data stored and/or accessed by computing device 200 can include private medical record information, or PHI, embodiments of the computing device 200 can be implemented utilizing secure data storage and access procedures.

Generally, in terms of the hardware architecture as shown in FIG. 2, computing device 200 includes processor 202, memory 204, user interface 208, and communication module 210. As will be appreciated, the user interface 208 may include one or more input devices (e.g., a keyboard, a mouse, a touch screen, etc.) and one or more output devices (e.g., a display, an audio speaker, etc.). As shown in FIG. 2, refill reminder module 206 may be stored in memory 204. In some embodiments, memory 204 may also store, all or in portion, authentication data 110 and/or prescription refill webpage 108 of FIG. 1.

Processor 202 is a hardware device and may include one or more data processing units, such as a central processing unit (CPU) and/or a graphics processing unit (GPU). Processor 202 may also represent multiple parallel or distributed processors working in unison. When computing device 200 is in operation, processor 202 is configured to execute software stored within memory 204, to communicate data to and from memory 204, and to generally control operations of computing device 200 pursuant to the software.

Memory 204 may be a computer-readable, non-transitory, data storage device that may include one or a combination of volatile memory elements (e.g., random access memory (RAM)) or nonvolatile memory elements (e.g., ROM, hard drive, flash drive, CDROM, etc.). In some cases, memory 204 may incorporate electronic, magnetic, optical, and/or other types of storage media. Memory 204 may have a distributed architecture where various components are situated remote from one another, but are still accessed by processor 202. These other components may reside on devices located elsewhere on a network or in a cloud arrangement. In some cases, memory 204 may be utilized to implement one or more databases 116.

Memory 204 is configured to store executable software, some of which may or may not be unique to the pharmacy system 102. The software in memory 204 may include one or more separate programs, each comprising an ordered listing of machine readable instructions that, when executed by processor 202, cause the processor 202 to perform various acts and/or implement logical functions. As an example, the software in memory 204 may include a suitable operating system (O/S) and the refill reminder module 206.

Refill reminder module 206 may be a portion of memory 204 that is configured to store software instructions that, when executed by the processor 202, cause the processor 202 to, among other things: (i) generate an authentication token associated with the user; (ii) generate a short URL based on a web address corresponding to a prescription refill webpage associated with the user, and incorporating the authentication token; (iii) provide, to a mobile device, a refill reminder message comprising the short URL; (iv) upon receiving a request to access the short URL, validate the request based on stored authentication data, (v) generating the prescription refill webpage based on the user's customer profile data; and (vi) provide access to the prescription refill webpage on the mobile device upon obtaining authorization to electronically access protected health information (PHI) of the user.

For purposes of communicating with other components of the environment 100 over the communication network 106 using any suitable number of wired and/or wireless links, computing device 200 is equipped with communication module 210. The communication module 210 may be configured to send and receive data over the communication network 106 using one or more network protocols, such as, for example, cellular network protocol, Internet protocol suite (TCP/IP), IEEE 802.11 Wi-Fi, etc. Accordingly, the communication module 210 comprises various network communication equipment and circuitry, such as, for example, a telephonic interface, a cellular communication port, a network interface, a network card, such as an Ethernet card or a wireless connection card, a router, any suitable number of wired and/or wireless transceivers, etc.

Figures 8, 9:
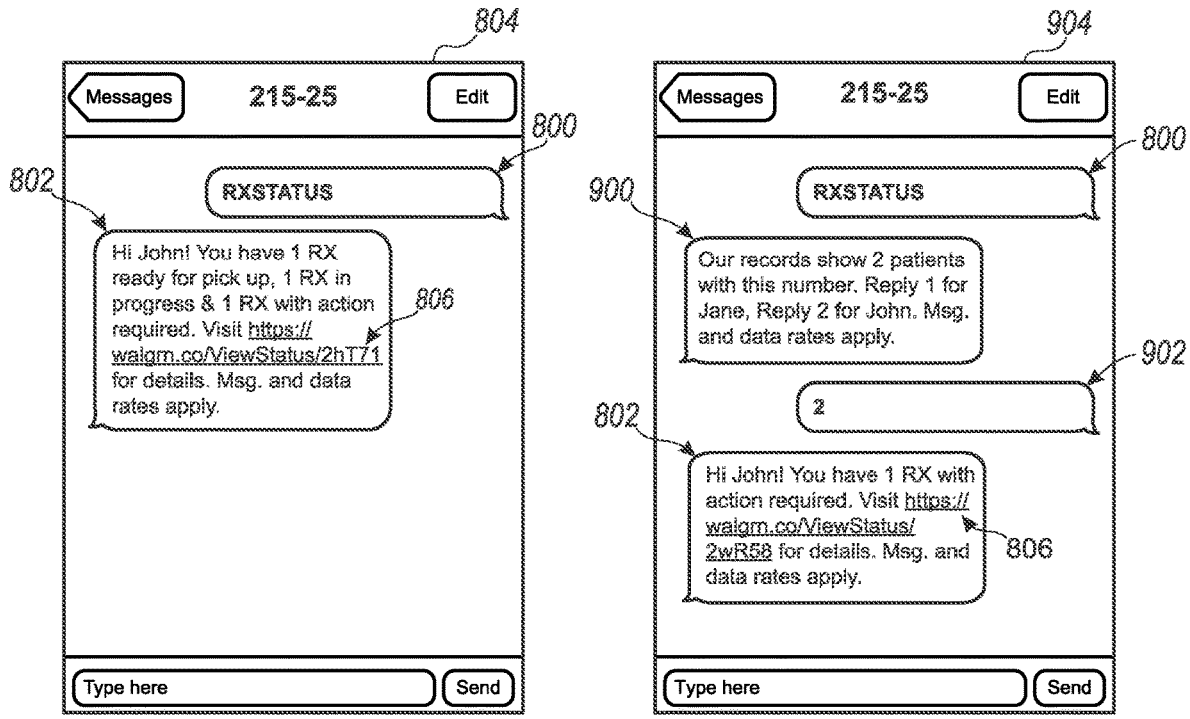
FIG. 8 is a screenshot of an exemplary refill status text message displayed on a mobile device of the environment of FIG. 1, in accordance with embodiments.
FIG. 9 is another screenshot of an exemplary refill status text message displayed on a mobile device of the environment of FIG. 1, in accordance with embodiments.

FIG. 8 illustrates an example screenshot of an refill status request 800 and a refill status message 802 displayed on a display screen 804 of a mobile computing device, such as the mobile device 104. As shown, the refill status request 800 may be entered through the graphical user interface of a mobile messaging application of the mobile device 104. In the illustrated example, the refill status request 800 states: "RXSTATUS." The refill status request 800 may include any suitable keyword defined by the pharmacy system 102 and/or the refill status module 212. In some examples, the pharmacy system 102 and/or the refill status module 212 may define multiple keywords that can be included in the refill status request 800 sent by the customer. For example, both "RXSTATUS" and "STATUSRX" may be valid keywords. The In the illustrated example, the refill status message 802 is displayed in the graphical user interface of a mobile messaging application of the mobile device 104. As also shown, the content of the refill status message 802 states: "Hi John! You have 1 RX ready for pickup, 1 RX in progress and 1 RX with action required," without identifying which medications are associated with customer. In response, the customer clicking on a user-selectable short URL, or hyperlink, 806 to view the prescription status in an external webpage before placing a refill order. The short URL of the hyperlink 806 can be configured to direct the customer to the prescription status webpage 122 associated with the customer, such as, for example, the prescription status webpage 1000 shown of FIG. 10.

FIG. 9 illustrates an example screenshot of a refill status request 800, a clarification message 900, a clarification response 902, and a refill status message 802 displayed on a display screen 904 of a mobile computing device, such as the mobile device 104. In the illustrated example, the refill status request 800 may be entered through the graphical user interface of a mobile messaging application of the mobile device 104. In the illustrated example, the refill status request 800: "RXSTATUS." In the illustrated example, because more than one customer is associated with the mobile device 104 in the database 116, the clarification message 900 is displayed in the graphical user interface of a mobile messaging application of the mobile device 104. In the illustrated example, the content of the clarification message 900 provides customer identifiers (e.g., "Jane" and "John") and temporary identifiers (e.g., "1" and "2"). The clarification message 900 may be entered through the graphical user interface of a mobile messaging application. The clarification message 900 may include one of the temporary identifiers provided in the clarification message 900. In the illustrated example, the refill status message 802 is displayed in the graphical user interface of a mobile messaging application of the mobile device 104. The content of the example refill status message 802 states: "Hi John! You have 1 RX with action required," without identifying which medications are associated with customer. In response, the customer clicking on a user-selectable short URL, or hyperlink, 806 to view the prescription status in an external webpage before placing a refill order. The short URL of the hyperlink 806 can be configured to direct the customer to the prescription status webpage 122 associated with the customer, such as, for example, the prescription status webpage 1000 shown of FIG. 10.

Figure 10:
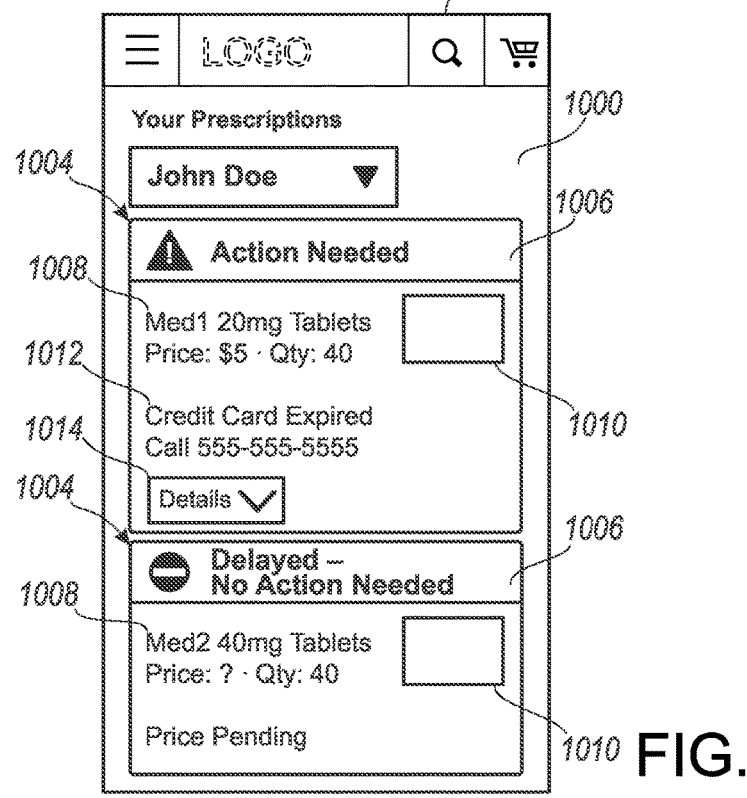
FIG. 10 is a screenshot of an exemplary prescription status webpage displayed on a mobile device of the environment of FIG. 1, in accordance with embodiments.

FIG. 10 illustrates an example screenshot of a prescription status webpage 1000 displayed on a display 1002 of a mobile computing device, such as the mobile device 104. In the illustrated example, the prescription status webpage 1000 displays prescription information 1004 for at least one drug, medicament, or medical device that is currently-prescribed to the user, or a patient associated with the user (e.g., a family member). In the illustrated example, the prescription information 1004 includes a status indicator 1006, a prescription summary 1008, a picture of the drug, medicament, or medical device 1010. In some examples, when the status indicates that the user needs to act before the prescription can be filled, the prescription information 1004 includes an action summary 1012 and/or an interface 1014 (e.g., a drop down menu, a URL, etc.) to direct the customer to a more detailed description of the issue.

Figure 11:
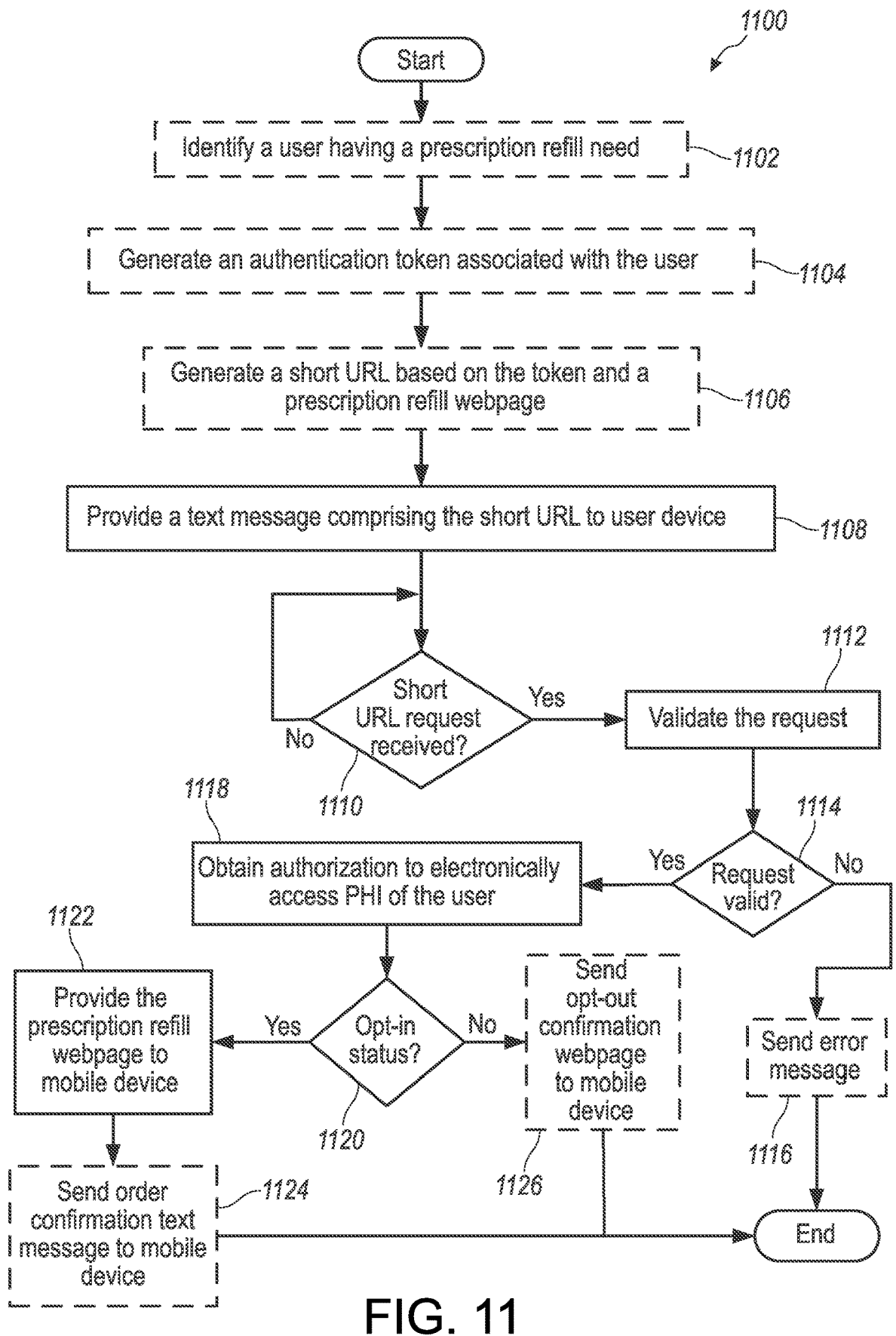
FIG. 11 is a flowchart illustrating an exemplary method for providing secure access to prescription refill information on a mobile device, in accordance with embodiments.

FIG. 11 illustrates a flowchart showing an exemplary method 1100 for providing secure electronic access to prescription refill information on a mobile device, in accordance with embodiments. In some embodiments, the method 1100 may be implemented by the pharmacy system 102 of FIG. 1, using software stored on a computer readable medium and executing on one or more computer processors of the pharmacy system 102. In some embodiments, the method 1100 may be carried out by the computing device 200 of FIG. 2, executing all or a portion of the refill reminder module 206 stored in the memory 204, using the processor 202. The pharmacy system 102 and/or the computing device 200 may interact with one or more components of the environment 100, including the mobile device 104 and/or the message delivery system 118, to carry out the operations of method 1100.

The method 1100 may begin at step 1102, where the processor identifies one or more users having a prescription refill need, and/or requiring a refill reminder message, based on prescription information stored in a database (e.g., database 116) of the pharmacy system 102, as described in more detail herein. For example, the processor may determine that a prescription refill is due based on the dosage and quantity of a currently-prescribed drug, the prescription order date, the number of available refills, and an expiration date of the available refills.

The method 1100 may further include step 1104, where the processor generate an authentication token for each identified user using customer profile data or other data associated with the user and retrieved from, for example, a pharmacy database (e.g., database 116), as described in more detail herein. For example, the authentication token may be generated based on identifying information associated with the user (e.g., patient ID number), contact information of the user (e.g., mobile phone number), and/or a reminder identifier (ID) assigned to the user for the purpose of identifying the refill reminder message being sent thereto. The authentication token may be generated using encryption, hashing, encoding, and/or other cryptography techniques. The authentication token may be stored in a data table (e.g., authentication data 110) stored in a memory of the pharmacy system (e.g., memory 204) for future retrieval. For example, the authentication token may be mapped to the data used to create the token (e.g., reminder ID, patient ID, mobile number, etc.), other customer profile data for the user (e.g., name), a hash value associated with the token, and/or an expiration date of the token.

The method 1100 may also include step 1106, where, for each identified user, the processor generates a short uniform resource locator (URL) based on an intended web address and the authentication token associated with the user. The web address may be a long URL corresponding to a prescription refill webpage configured for the user based on the customer profile data of the user (e.g., prescription refill webpage 400 in FIG. 4). The short URL may include a shortened domain name corresponding to the original domain name included in the long URL and a string of characters uniquely associated with the user. In addition, the authentication token generated for the user may be embedded into the short URL for security purposes. The short URL may be stored in the data table in association with the authentication token data and customer profile data stored therein for the corresponding user. In some cases, the long URL may also be stored in the data table.

At step 1108, the processor provides a refill reminder message comprising the short URL to a mobile device (e.g., mobile device 104) of each user having a prescription refill need. The short URL may be presented within the refill reminder message as a user-selectable link (e.g., hyperlink 304 in FIG. 3). The refill reminder message may be provided to the mobile device over a communication network (e.g., communication network 106) as an SMS text message (e.g., refill reminder text message 300 in FIG. 3) or an email message that may be delivered as a text message.

In some cases, the processor provides the content of each refill reminder message and the user's contact information (e.g., mobile number, email address, etc.) to a third-party message delivery service (e.g., message delivery system 118) for distribution to the identified users. For example, the processor may send the data table comprising the authentication token data (e.g., token, hash value, expiration date, etc.), customer profile data (e.g., name, mobile number, etc.), and corresponding short URLs for all identified users to the message delivery service. The message delivery service may generate a refill reminder message for each user based on corresponding data in the data table and send the generated message to the mobile number associated with the user.

At step 1110, the processor determines whether a request to access the short URL has been received. For example, upon receiving the refill reminder message, the user may click on the short URL link within the message to access the prescription refill webpage of the user, and in response, the mobile device may send a request to access the short URL to the processor. At step 1110, the method 1100 may continue to check for a short URL request until one is received.

Once a request is received, the method 1100 continues to step 1112, where the processor validates the request based on stored authentication data. For example, the process may compare authentication information included in the request to the authentication token data, including the hash value and expiration date, stored in the data table. The request may be determined to be valid if the authentication information matches the stored authentication data and/or the authentication token has not expired. At step 1114, the processor determines whether the request is valid based on the comparison performed at step 1112. If the request is not valid, at step 1116 the processor sends an error message to the mobile device indicating that the short URL request could not be validated.

If the request is valid, the method 1100 continues to step 1118, where the processor obtains authorization from the user to electronically access the protected health information (PHI) of the user. In some cases, the processor obtains PHI authorization by providing a PHI access webpage (e.g., PHI access webpage 500 in FIG. 5) to the mobile device requesting the user to grant PHI authorization. The PHI access webpage may include an identity verification prompt (e.g., prompt 504 in FIG. 5) that requests the user to enter identity verifying information (e.g., date of birth), a terms and conditions prompt (e.g., check box 508 in FIG. 5) that requests the user to accept the terms and conditions associated with providing PHI authorization, and a submit option (e.g., submit option 506) that submits the user's PHI authorization and identity verification information to the processor. The processor may verify the user identity data received via the PHI access webpage based on stored customer profile data (e.g., date of birth).

If the user's identity is verified, the processor may assign an opt-in status to the user in the stored user profile data, for example, in a PHI indicator field of the user's profile. In addition, the processor may provide a web cookie (e.g., web cookie 120 in FIG. 1) to the mobile device for storage thereon. The web cookie may indicate the opt-in status of the user and may include authentication information (e.g., a token). The processor may store the web cookie and its authentication information in the data table in association with the other refill reminder data of the user for future retrieval. The mobile device may store the web cookie in a web browser or pharmacy application of the mobile device and provide the web cookie with each short URL request thereafter to indicate the previously-provided PHI authorization. As a result, for future short URL requests, the processor may obtain PHI authorization by validating the web cookie received with the request to access the short URL based on the stored cookie data.

At step 1120, the processor determines whether the user's profile data indicates an opt-in status for the user, either based on receipt of a web cookie with the short URL request or upon receiving authorization through the PHI access webpage. If an opt-in status is found, at step 1122 the processor provides access to the prescription refill webpage associated with the short URL on the mobile device. If the user decides to submit a prescription refill order via the prescription refill webpage, the method 1100 may also include step 1124, where the processor sends an order confirmation message to the mobile device of the user. As an example, the order confirmation message may be an SMS text message sent to the mobile number of the user or an email message. The method 1100 may end after the refill order is complete.

In some cases, the user may decide to opt-out of providing PHI authorization. In such cases, at step 1120, the processor may determine that an opt-in status is not present and/or that the user has been assigned an opt-out status. For example, the processor may assign an opt-out status to the user in the stored user profile data upon receiving user-selection of an option (e.g., opt-out option 410) to not authorize access to the PHI of the user from the mobile device. If opt-out status is determined, the method 1100 may include step 1126, where the processor sends an opt-out confirmation webpage (e.g., webpage 700 in FIG. 7) to the mobile device. In such cases, the method 1100 may end once the user receives opt-out confirmation.

Figure 12:
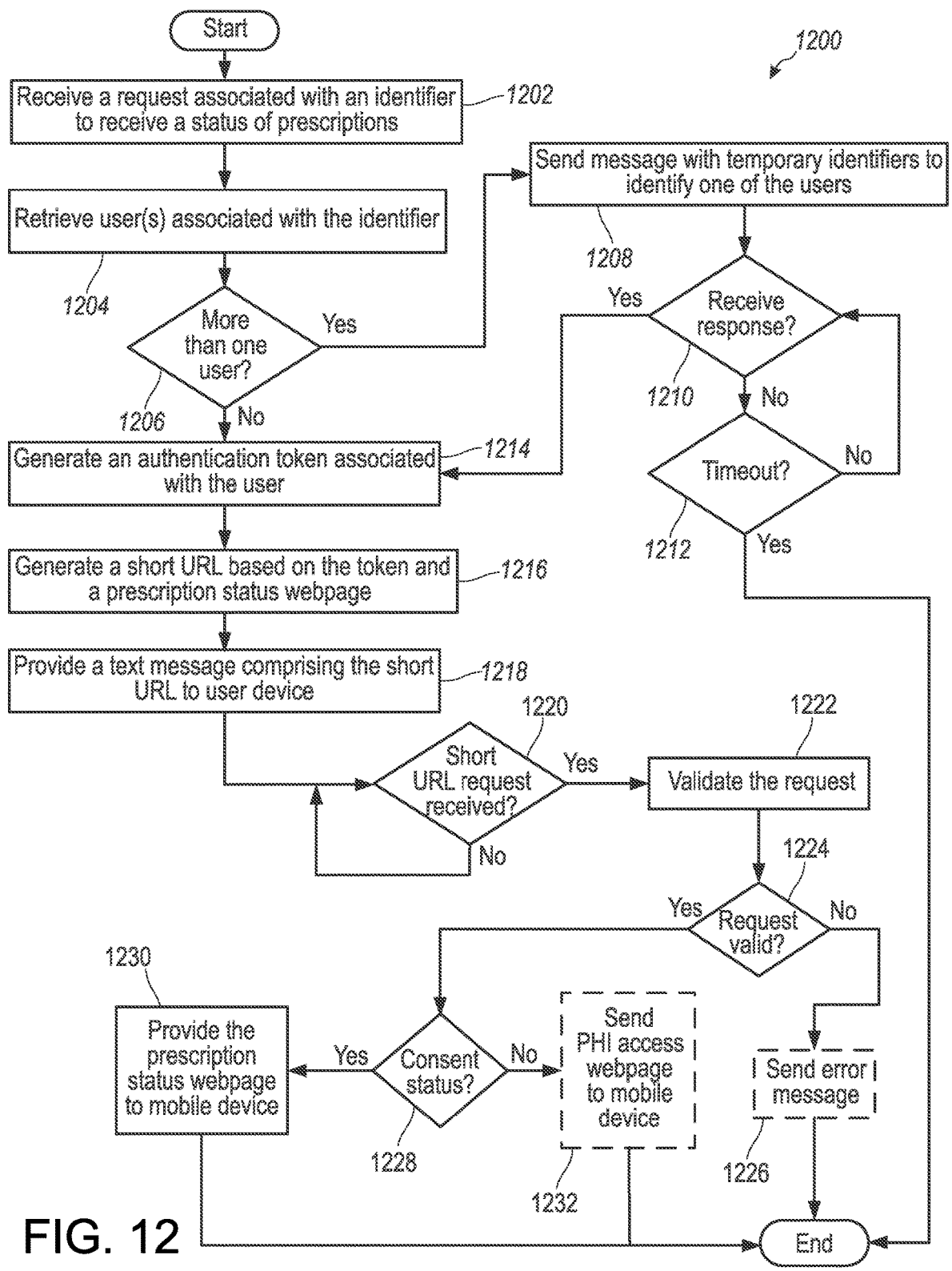
FIG. 12 is a flowchart illustrating an exemplary method for providing secure access to prescription status information on a mobile device, in accordance with embodiments.

FIG. 12 illustrates a flowchart showing an exemplary method 1200 for providing secure electronic access to prescription status information on a mobile device (e.g., the mobile device 104 of FIG. 1). In some embodiments, the method 1200 may be implemented by the pharmacy system 102 of FIG. 1, using software stored on a computer readable medium and executing on one or more computer processors of the pharmacy system 102. In some embodiments, the method 1200 may be carried out by the computing device 200 of FIG. 2, executing all or a portion of the refill status module 212 stored in the memory 204, using the processor 202. The pharmacy system 102 and/or the computing device 200 may interact with one or more components of the environment 100, including the mobile device 104 and/or the message delivery system 118, to carry out the operations of method 1200.

Initially, at step 1202, the computing device 200 receives a request message (e.g., the refill status request 800 of FIGS. 8 and 9). The request message includes a word and/or phrase, and is associated with an identifier (e.g., a telephone number, a MAC address, an IP address, an ESN, a MEID, an 'MEI, a LRN, an MIN, etc.) for identifying the mobile device 104 from which the request message was sent. The computing device 200 compares the word and/or phrase in the message to one or more keywords associated with requesting the status of prescriptions. The computing device 200 ignores messages that do not contain the keywords.

At step 1204, the computing device 200 searches the database 116 to retrieve the user(s) corresponding to the identifier associated with the request message received at step 1202. At step 1206, the computing device 200 determines if there is more than one user to the identifier associated with the request message received at step 1202. If there is more than one user, the method 1200 continues to step 1208. If there is one user, the method continues to step 1214.

At step 1208, the computing device 200 sends a clarification message (e.g., the clarification message 900 of FIG. 9) to the mobile device 104 with (a) temporary identifiers associated with each of the users identified at step 1204 and (b) user identifiers associated with each of the users identified at step. For example, the clarification message may state: "Our records show 2 people associated with this number. Reply 1 of Jane. Replay 2 of John." At step 1210, the computing device 200 determine whether a clarification response (e.g. the clarification reply 902 of FIG. 9) that contains one of the temporary identifier has been received from the mobile device 104 associated with the request message received at step 1202. If the computing device 200 has received the clarification response that contains one of the temporary identifier, the method 1200 continues at step 1214. Otherwise, if the computing device 200 has not received the clarification response that contains one of the temporary identifier from the mobile device 104, the method continues at step 1212. At step 1212, the computing device 200 determines whether a timer set when the clarification message was sent has timed out. If the timer has not timed out, the method 1200 returns to step 1210. Otherwise, if the time has timed out, the method 1200 ends.

At step 1214, the computing device 200 generates an authentication token for the user identified at step 1204 or step 1210 using customer profile data or other data associated with the user and retrieved from, for example, a pharmacy database (e.g., database 116). For example, the authentication token may be generated based on identifying information associated with the user (e.g., patient ID number), contact information of the user (e.g., mobile phone number), and/or a status identifier (ID) assigned to the user for the purpose of identifying the refill status message being sent thereto. The authentication token may be generated using encryption, hashing, encoding, and/or other cryptography techniques. The authentication token may be stored in a data table (e.g., authentication data 110) stored in a memory of the pharmacy system (e.g., memory 204) for future retrieval. For example, the authentication token may be mapped to the data used to create the token (e.g., reminder ID, patient ID, mobile number, etc.), other customer profile data for the user (e.g., name), a hash value associated with the token, and/or an expiration date of the token.

At step 1216, computing device 200 generates, for the user, a short uniform resource locator (URL) based on an intended web address and the authentication token associated with the user. The web address may be a long URL corresponding to a prescription status webpage configured for the user based on the customer profile data of the user (e.g., prescription status webpage 1000 of FIG. 10). The short URL may include a shortened domain name corresponding to the original domain name included in the long URL and a string of characters uniquely associated with the user. In addition, the authentication token generated for the user may be embedded into the short URL for security purposes. The short URL may be stored in the data table in association with the authentication token data and customer profile data stored therein for the corresponding user. In some cases, the long URL may also be stored in the data table.

At step 1218, the computing device 200 provides a refill status message comprising the short URL to a mobile device (e.g., mobile device 104) of the user. The short URL may be presented within the refill status message as a user-selectable link (e.g., the hyperlink 806 of FIGS. 8 and 9). The refill status message may be provided to the mobile device over a communication network (e.g., communication network 106) as an SMS text message (e.g., refill status text message 802 of FIGS. 8 and 9) or an email message that may be delivered as a text message.

At step 1220, the computing device 200 determines whether a request to access the short URL has been received. For example, upon receiving the refill status message, the user may click on the short URL link within the message to access the prescription status webpage of the user, and in response, the mobile device may send a request to access the short URL to the processor. At step 1220, the method 1200 may continue to check for a short URL request until one is received.

Once a request is received, the method 1200 continues to step 1222, where the computing device 200 validates the request based on stored authentication data. For example, the process may compare authentication information included in the request to the authentication token data, including the hash value and expiration date, stored in the data table. The request may be determined to be valid if the authentication information matches the stored authentication data and/or the authentication token has not expired. At step 1224, the computing device 200 determines whether the request is valid based on the comparison performed at step 1222. If the request is not valid, at step 1226 the computing device 200 sends an error message to the mobile device indicating that the short URL request could not be validated.

At step 1228, the computing device 200 determines whether the user's profile data indicates consent by the user to access the user's PHI, either based on receipt of a web cookie with the short URL request or upon receiving authorization through the PHI access webpage. If an opt-in status is found, at step 1230 the computing device 200 provides access to the prescription status webpage associated with the short URL on the mobile device. The method 1200 may end after the prescription status webpage is visited.

In some cases, the user may decide to opt-out of providing PHI authorization. In such cases, at step 1232, the computing device 200 may determine that an authorization is not present and/or that the user has been assigned an opt-out status. For example, the computing device 200 may assign an opt-out status to the user in the stored user profile data upon receiving user-selection of an option (e.g., opt-out option 410) to not authorize access to the PHI of the user from the mobile device. If opt-out status is determined, the method 1200 may include step 1134, where the computing device 200 sends an PHI access webpage (e.g., webpage 500 of FIG. 5) to the mobile device. In such cases, the method 1200 may end.

In certain embodiments, the process descriptions or blocks in the figures, such as FIGS. 11 and 12, can represent modules, segments, or portions of code which include one or more executable instructions for implementing specific logical functions or steps in the process. Any alternate implementations are included within the scope of the embodiments described herein, in which functions may be executed out of order from that shown or discussed, including substantially concurrently or in reverse order, depending on the functionality involved, as would be understood by those having ordinary skill in the art.

It should be emphasized that the above-described embodiments of the invention, particularly, any "preferred" embodiments, are possible examples of implementations, merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and the invention and protected by the following claims.

What is claimed:

1. A computer-implemented method of providing secure electronic access to prescription status information of a user, the method comprising:
   transmitting, via one or more processors, a text message including a short uniform resource locator (URL) to a mobile computing device associated with the user, wherein the short URL includes a secure authentication token;
   receiving, in response to a selection of the user, the secure authentication token in a pharmacy system;
   transmitting, when the secure authentication token matches stored authentication data, a prescription refill webpage to the mobile computing device;
   receiving, in response to a selection of the user, a prescription refill order request in the pharmacy system; and
   transmitting, in response to receiving the prescription refill order request, a refill order confirmation to the mobile device of the user.

2. The computer-implemented method of claim 1, wherein the stored authentication data includes a hash value associated with the secure authentication token and an expiration date associated with the secure authentication token.

3. The computer-implemented method of claim 1, further comprising:
   validating the prescription order refill request by comparing authentication information included in the request to the stored authentication data.

4. The computer-implemented method of claim 1, further comprising:
   obtaining authorization to electronically access protected health information (PHI) of the user by validating, via the one or more processors, a web cookie.

5. The computer-implemented method of claim 1, further comprising:
   providing, over a communication network, a PHI access webpage to the mobile device;

verifying, via the one or more processors, user identity data received via the PHI access prompt based on stored user profile data; and authorizing electronic access to PHI of the user by assigning, by the one or more processors, an opt-in status to the user in the stored user profile data.

6. The computer-implemented method of claim 5, further comprising:

providing, over the communication network, the web cookie to the mobile device for storage thereon, the web cookie indicating the opt-in status of the user.

7. The computer-implemented method of claim 1, wherein determining the user corresponding the mobile device associated with the status request message includes:

comparing, via the one or more processors, an identifier associated with the mobile device to user profile data to identify potential users;

in response to identifying more than one potential user in the user profile data, providing, over the communication network, a clarification message comprising temporary identifiers associated with each of the potential users corresponding to the mobile device; and in response to receiving a clarification response from the mobile device, selecting the one of the potential users as the user based on the temporary identifier in the clarification response.

8. A non-transitory computer readable storage medium including computer-executable instructions that, when executed by one or more processors, cause a computer to:

determine, in response to receiving a status request message, a user corresponding to a mobile device associated with the status request message;

provide, over a communication network, a refill status message comprising a short uniform resource locator (URL) to the mobile device associated with the status request message, wherein the short URL includes a secure authentication token;

receive a request to access the short URL;

validate the request based on stored authentication data; and provide, over the communication network, access to the prescription status webpage on the mobile device upon obtaining authorization to electronically access protected health information (PHI) of the user.

9. The non-transitory computer readable storage medium of claim 8, wherein the stored authentication data includes a hash value associated with the authentication token and an expiration date associated with the token, and wherein validating the request includes comparing, via the one or more processors, authentication information included in the request to stored authentication data.

10. The non-transitory computer readable storage medium of claim 8, wherein obtaining authorization to electronically access PHI of the user includes validating a web cookie received with the request to access the short URL.

11. The non-transitory computer readable storage medium of claim 8, wherein obtaining authorization to electronically access PHI of the user includes:

providing, over the communication network, a PHI access webpage to the mobile device;

verifying user identity data received via the PHI access webpage based on user profile data stored in the data storage device; and assigning an opt-in status to the user in the stored user profile data.

12. The non-transitory computer readable storage medium of claim 8, wherein the instructions further cause the computer to provide, over the communication network, a web cookie to the mobile device for storage thereon, the web cookie indicating the opt-in status of the user.

13. The non-transitory computer readable storage medium of claim 8, wherein to determine the user corresponding to the mobile device associated with the status request message, the instructions further cause the computer:

compare an identifier associated with the mobile device to user profile data to identify potential users;

in response to identifying more than one potential user in the user profile data, provide, over the communication network, a clarification message comprising temporary identifiers associated with each of the potential users corresponding to the mobile device; and in response to receiving a clarification response from the mobile device, select the one of the potential users as the user based on the temporary identifier in the clarification response.

14. A system in network communication with a mobile device of a user, the system comprising:

one or more processors;

one or more memories storing computer-executable instructions that, when executed by the one or more processors, cause the system to:

determine, in response to receiving a status request message, an identity of the user corresponding the mobile device associated with the status request message;

provide, over a communication network, a refill status message comprising a short uniform resource locator (URL) to the mobile device associated with the status request message, the short URL including a secure authentication token;

upon receiving a request to access the short URL, validate the request based on stored authentication data; and provide, over the communication network, access to the prescription status webpage on the mobile device upon obtaining authorization to electronically access protected health information (PHI) of the user.

15. The system of claim 14, wherein the stored authentication data comprises a hash value associated with the authentication token and an expiration data associated with the token.

16. The system of claim 14, wherein validating the request includes comparing authentication information included in the request to the stored authentication data.

17. The system of claim 14, wherein obtaining authorization to electronically access PHI of the user includes validating a web cookie received with the request to access the short URL.

18. The system of claim 14, wherein obtaining authorization to electronically access PHI of the user includes:

providing a PHI access webpage to the mobile device;

verifying user identity data received via the PHI access prompt based on user profile data stored in the memory; and assigning an opt-in status to the user in the stored user profile data.

19. The system of claim 18, the memories including further computer-executable instructions that, when executed by the one or more processors, cause the system to:

provide a web cookie to the mobile device for storage thereon, the web cookie indicating the opt-in status of the user.

20. The system of claim 14, the memories including further computer-executable instructions that, when executed by the one or more processors, cause the system to:
   compare an identifier associated with the mobile device to user profile data to identify potential users;
   in response to identifying more than one potential user in the user profile data, provide, over the communication network, a clarification message comprising temporary identifiers associated with each of the potential users corresponding to the mobile device; and
   in response to receiving a clarification response from the mobile device, select the one of the potential users as the user based on the temporary identifier in the clarification response.

\* \* \* \* \*